United States Patent [19]  [11] 3,983,289
Nishizaki et al.  [45] Sept. 28, 1976

[54] ELECTRICALLY INSULATING PREPREG

[75] Inventors: Syunichiro Nishizaki; Hiroshi Teratani; Osamu Fujisawa; Jiro Fukushima, all of Amagasaki; Makoto Tokizawa, Kawasaki; Nobukatsu Wakabayashi, Kawasaki; Takashi Saito, Kawasaki, all of Japan

[73] Assignees: Mitsubishi Chemical Industries Ltd.; Mitsubishi Denki Kabushiki Kaisha, both of Tokyo, Japan

[22] Filed: Apr. 9, 1974

[21] Appl. No.: 459,316

[30] Foreign Application Priority Data

Apr. 9, 1973  Japan.............................. 48-40185
May 25, 1973  Japan.............................. 48-58397
Aug. 2, 1973  Japan.............................. 48-86974

[52] U.S. Cl.............................. 428/268; 260/78.41; 427/386; 427/390; 427/391; 427/392; 428/290; 428/324; 428/413; 428/417; 428/454
[51] Int. Cl.² ...................... B32B 7/00; B32B 17/02
[58] Field of Search.......... 117/123 D, 154, 161 ZB; 260/78.4 EP; 428/268, 290, 324, 413, 417, 454; 427/386, 390, 391, 398

[56] References Cited

UNITED STATES PATENTS

| 3,218,370 | 11/1965 | Fry et al. | 117/161 |
| 3,305,417 | 2/1967 | Christie | 117/161 |
| 3,476,693 | 11/1969 | Mango et al. | 117/161 |
| 3,493,414 | 2/1970 | Hastings | 117/161 |
| 3,557,035 | 1/1971 | Schmid et al. | 117/161 |
| 3,565,861 | 2/1971 | White et al. | 117/161 |
| 3,632,427 | 1/1972 | Green | 117/123 |
| 3,728,306 | 4/1973 | Markovitz et al. | 117/123 |
| 3,790,532 | 2/1974 | Fukutani et al. | 260/78.4 |

Primary Examiner—Ronald H. Smith
Assistant Examiner—Sadie L. Childs
Attorney, Agent, or Firm—Oblon, Fisher, Spivak, McClelland & Maier

[57] ABSTRACT

An electrically insulating prepreg which comprises a resin composition of an alicyclic epoxy compound prepared by the expoxidation of an alkadiene alcohol ester of an alicyclic polybasic carboxylic acid, a latent curing agent, and a solid substrate, wherein said resin composition, once it has been applied to the substrate, is in the B-stage cured state and is thereby acetone soluble, thermoplastic and nontacky.

10 Claims, No Drawings

ELECTRICALLY INSULATING PREPREG

BACKGROUND OF THE INVENTION

1. Field of the Invention

The present invention relates to electrically insulating prepregs which have excellent adhesive and thermal resistance properties, excellent mechanical strength and electrical insulating properties and especially good tracking resistance.

2. Description of the Prior Art

Generally, electrically insulating prepregs are used for the preparation of various shapes of laminated products such as laminated boards, laminated rods and laminated tubes by molding the prepreg or by preparing an electrical insulated conductor by coating or encapsulating the conductive material. The electrically insulating prepregs preferably are not very tacky at room temperature and are stable upon storage over long periods of time.

Among the necessary properties which the laminated products prepared from the electrically insulating prepregs must possess are satisfactory electrical and mechanical properties and good adhesive and thermal resistance. Because electrical instruments are now being used in high voltage applications in outdoor or indoor polluted environments, it is necessary that they maintain excellent characteristics under these conditions. The laminated products used in these electrical instruments are required to have arc and tracking resistance characteristics which prevent a decrease in the electrical insulating properties of the instruments. Such losses in electrically insulating properties can occur by the formation of conductive passages resulting from the deposition of carbon by current discharges or leaking currents on the surface of the laminated products. In other words, the properties of the laminated products prepared from the prepregs, of course, include the properties of the prepregs. However, laminated products derived from the conventional electrically insulating prepregs have not had satisfactory properties because the properties of the prepregs have not been satisfactory.

The known electrically insulating prepregs have been prepared from phenol resins, epoxy resins, unsaturated polyester resins, diphenyloxide resin and aniline, B-stage resins impregnated into solid substrates and the like. Coventional prepregs have good adhesive and mechanical properties. However, the laminated products and the molded products prepared from the conventional prepregs have disadvantageously low electrical properties especially, low arc resistance and tracking resistance. This results in products which do not possess long life with regard to their insulating properties as electrical insulators for electrical instruments for use in outdoor or in polluted environments. The laminated products prepared from the conventional melamine resin prepregs have good arc resistance and tracking resistance. However, they have the disadvantages of being brittle, low thermal resistance and cracks are easily formed on the surface. The laminated products prepared from the conventional silicon resin prepregs have good thermal resistance, arc resistance and tracking resistance. However, the silicon resin prepregs have low adhesive and low mechanical strengths.

In an approach to solve the problems associated with the prepregs, it was believed that prepregs could be prepared by impregnating a solid substrate such as a fibrous substrate, sheet-like substrate or a complex substrate wth a resin composition of an alicyclic epoxy resin which had no aromatic rings in the molecules and a curing agent. In order to confirm this hypothesis, studies have been conducted in which prepregs were prepared from solid substrates and various resin compositions which contained various curing agents and various commercial alicyclic epoxy resins, such as Chissonox 221 manufactured by Chisso Co., and Araldite CY-183 manufactured by Ciba-Geigy Co. However, with these resins it was very difficult obtaining a stable B-stage condition.

A need therefore, continues to exist for pregregs which can be formed from stable B-stage resins which have excellent storage stability, whereby the laminated or coated products prepared from the prepregs have satisfactory adhesive, thermal resistance, mechanical and electrical characteristics and especially, high arc resistance and tracking resistance.

SUMMARY OF THE INVENTION

Accordingly, one object of the present invention is to provide an electrical insulating prepreg which has excellent storage stability and adhesive properties and whose laminated or coated products possess excellent thermal resistance, mechanical characteristics and electrical characteristics and especially high arc resistance and tracking resistance.

Briefly, this object and other objects of the invention as hereinafter will become more readily apparent can be attained by providing an electrically insulating prepreg which comprises a resin composition of an alicyclic epoxy compound prepared by the epoxidation of an alicyclic polybasic carboxylic ester derived from an alkadiene alcohol, a latent during agent and a solid substrate, wherein the resin composition is in the B-stage cured state once it has been applied to the substrate and is characterized by being acetone soluble, thermoplastic and nontacky.

DETAILED DESCRIPTION OF THE PREFERRED EMBODIMENTS

The alicyclic polybasic carboxylic esters used in the present invention can be prepared by the esterification of an alkadiene alcohol with an alicyclic polybasic carboxylic acid or anhydride. The alicyclic polybasic carboxylic esters can also be prepared by an ester interchange reaction of an alkyl ester of an alicyclic polybasic carboxylic acid. Suitable alkadiene alcohols include 2,7 - octadienol - 1, and 1, 7 - octadienol - 3. These alkadiene alcohols can be prepared by the methods disclosed in Japanese Patent Publication No. 46045/1972 and Japanese Patent Publication No. 27487/1972. It is also possible to include allyl alcohol, octenyl alcohol or crotyl alcohol with the alkadiene alcohol. Suitable alicyclic polybasic carboxylic acids include tetrahydrophthalic acid, methyltetrahydrophthalic acid, hexahydrophthalic acid, nadic acid, endo-cisbicyclo[2.2.1]hept-5-ene-2,3-dicarboxylic acid, dihydronadic acid, and the like.

The alicyclic epoxy compounds used in the invention can be prepared by the epoxidation of the alicyclic polybasic carboxylic ester by the methods disclosed in Japanese Patent Publication No. 37007/1973 and British Pat. No. 1,316,379. The epoxidation reaction can be conducted by reacting 0.6 14 1.5 equivalents of an epoxidizing agent with the ester at 0° - 60°C, preferably 0° 40°C. The epoxidizing agents include peroxides such as peracetic acid, performic acid, perbenzoic acid and the like and hydrogen peroxide.

The alicyclic epoxy compound can be hydrogenated, if necessary, after the epoxidation to saturate the unepoxidized carbon-carbon double bonds in the epoxy compound. The weather durability of the cured product can be improved by the hydrogenation of the unsaturated carbon-carbon bonds.

The particular alicyclic epoxy compound employed can be selected by the appropriate choice of the alkadiene alcohol and the conditions of the epoxidation reaction. For example, alicyclic epoxy compounds having epoxy values ranging from 0.3 – 0.9 mole equivalent per 100g, and hydroxyl values of 0 – 0.2 mole equivalent per 100g can be prepared. In the invention, alicyclic epoxy compounds are preferably used which have epoxy values of 0.4 – 0.8 mole equivalent per 100g and hydroxyl values of 0.01 – 0.1 mole equivalent per 100g.

In the invention, uniform epoxy resin compositions (one liquid type) can be prepared by combining the alicyclic epoxy compound and the latent curing agent. Suitable latent curing agents include salts of Lewis acids, Lewis bases, salts of Lewis bases, urea-like compounds and derivatives thereof. The salts of Lewis acids include complexes of Lewis acids and amines, complexes of Lewis acids and phosphine, complexes of Lewis acids and phosphite and organotin compounds. Suitable Lewis acids used in the preparation of the salts of the Lewis acids include boron trifluoride, boron trichloride, aluminum chloride, aluminum bromide, ferric chloride, antimony chloride, stannic chloride, boron trialkoxide, aluminum trialkoxide, cupric chloride, cupric sulfate, nickel chloride, phosphorus pentafluoride, arsenic pentafluoride, antimony pentafluoride, and the like. The Lewis acid can be used by itself. However, it is preferable to use the Lewis acid dissolved in an ether, alcohol, ketone, dimethylformamide or the like solvent.

Suitable amines include aliphatic and alicyclic amines such as monomethyl amine, monoethyl amine, triethyl amine, monoethanol amine, triethanol amine, N-methylethanol amine, isopropanol amine, N, N - diphenylethanol amine, cyclohexyl amine; aromatic amines such as aniline, N,N-dimethylaniline, 2,4,6-tris[dimethyl-aminomethyl]phenol, benzylamine and the like; heterocyclic amines such imidazole, 2-ethyl-4-methylimidazole, cyanoethyl imidazole, morpholine, piperazine, pyridine, piperizine, triethylenediamine (1,4-diazabicyclo - [2,2,2]octane) and the like. Suitable phosphines include triphenylphosphine, tributylphosphine, tricyclohexyl phosphine and the like and the phosphites include trimethyl phosphite, triethyl phosphite, triphenyl phosphite and the like. Suitable organotin compounds include dibutyl-tin dilaurate, dibutyl-tin maleate, dimethyl-tin dioctoate, dimethyl-tin dihexoate and the like.

Suitable Lewis bases include ketimines (condensates of ketones such as acetone and methylethylketone with amines such as ethylenediamine and diethylenetriamine), imidazole, 2-ethyl-4-methylimidazole, cyanoethylimidazone and hydrazides such as isophthalic hydrazide, adiphichydrazide, sebatic dihydrazide, and the like. Suitable salts of Lewis bases include halides, organic acid salts, borates, quaternary ammonium and quaternary phosphonium silicates; organic acid salts of tertiary amines; imidazoles and organic acid salt and complex metal salt derivatives thereof. Suitable salts of Lewis bases include trimethylbenzyl ammonium chloride, tetraethylammonium bromide, trimethylbenzylammonium hexoate, tetramethylammonium tetraphenyl borate, tetrabutyl ammonium silicate, benzyltriphenylphosphonium chloride, triethylammonium acetate, the 2-ethyl hexoate salt of 2,4,6-tris[dimethylaminomethyl]phenol, trimellitic imidazole, and the like. Besides urea, the urea-like compounds and derivatives thereof include urea, thiourea, dicyanodiamide, guanidine salts, acetylguanidine and the like. The compound can be combined with the Lewis Acid.

In the invention, the alicyclic epoxy compound is mixed with the latent curing agent to form the epoxy resin composition (one liquid type). When the components are mixed, it is preferable to add the latent curing agent dropwise with stirring to the alicyclic epoxy compound at moderate temperatures. It is possible to use a solvent such as isopropanol, n-butanol, tert-butanol, acetone, methyl ethyl ketone, methyl cellosolve, butyl cellosolve, dimethylformamide, benzene, toluene, xylene, or the like in the mixing operation to control the viscosity of the composition. The temperature of the mixing operation can be room temperature to 80°C, preferably room temperature to 50°C. If the temperature of the mixing operation is too high, excess polymerization occurs by ring cleavage of the oxirane ring by the latent curing agent, and control of the polymerization reaction is not easy. In the mixing operation, less than 30% of the oxirane rings of the alicyclic epoxy compounds cause ring-cleavage.

The viscosity of the epoxy resin composition (one liquid type) increases depending upon the ring cleavage of the oxirane rings which decreases the epoxy values. Accordingly, the mixing conditions are controlled depending upon the purpose intended for the prepreg.

For example, when the alicyclic epoxy resin composition is used to coat a substrate, ring cleavage of 10 – 20% of the oxirane rings is preferable, and when the alicyclic epoxy resin composition is used for impregnation in a fibrous substrate, a lesser extent of cleavage is preferable.

The latent curing agent is usually used in ratios of 0.1 – 20 parts by weight per 100 parts by weight of the alicyclic epoxy compound (0.1 – 20 PHR, preferably 1 – 10 PHR). When the ratio is described in terms of mole percent based on the oxirane ring content, about 0.1 – 20 mole percent of the latent curing agent is used. Generally, as the amount of the latent curing agent used is increased, the degree of ring cleavage of the oxirane rings is increased. Therefore, the amount of the latent curing agent used is not too much. On the other hand, if the amount of the latent curing agent is decreased, the degree of ring cleavage of the oxirane rings is decreased, and the epoxy resin composition (one liquid type) having a low viscosity can be obtained. However, long heat treatment periods are required for the preparation of the final cured product or else the product is incompletely cured. Generally, 2 – 6 PHR of the latent curing agent is preferably added.

The electrically insulating prepreg of the invention is prepared by impregnating into or coating the alicyclic epoxy compound composition onto a solid substrate, and converting the composition to the B-stage at which stage the resin is acetone soluble, thermoplastic and perferably nontacky.

The solid substrates include fibrous substrates, sheet-like substrates and their complex substrates. Suitable fibrous substrates include organic and inorganic fibrous materials such as cloth, mat, paper, non-woven fabrics made of natural fibers such as cellulose, cotton, silk, hemp; synthetic fibers such as rayon, polyvinylalcohol(vinylone), polyester, nylon; inorganic fibers such as asbestos, glass fiber, whisker(mono crystal fibers of calcium sulfate, sodium aluminate, and the like).

When an inorganic fiber, especially a glass fiber is used, the surface of the substrate can be treated in order to improve the surface adhesiveness of the substrate. Suitable treatments include silane treatments and boron treatments.

Suitable sheet-like substrates include mica wrappers, mica paper, and the like.

In the preparation of the prepregs of the invention, the substrate is dipped in the alicyclic epoxy compound composition, and if a solvent is used, the solvent is removed, thereafter, the composition is converted to the desired B-stage by a suitable heat treatment under suitable temperature and time conditions.

The temperature of the heat treatment is usually 70° - 160°C, preferably 90° - 140°C. The desired prepreg can easily be obtained by the heat treatment. The time for the heat treatment depends upon the temperature and is usually 1 - 120 minutes.

The alicyclic epoxy resin composition in the B-stage is in the semi-cured condition which is not a final cured state (C-stage which is characterized by acetone insolubility and non-thermoplasticity) nor an uncured state (liquid A-stage).

The prepreg is thermoplastic and when the prepreg is heated, the prepreg becomes thermoplastic for a short time and reaches a C-stage thermosetting state by the ring opening polymerization caused by the ring cleavage of the oxirane ring.

The prepreg is substantially solvent soluble. The B-state cured state (semi-cured condition) is clearly different from the A-stage or liquid form (uncured condition) and from the C-stage or solvent insoluble and non-thermoplastic form (final cured condition). The solvents used to measure the solubility of the resins are the same as mentioned above, especially acetone and toluene.

The prepreg comprising the solid substrate and the alicyclic epoxy resin composition can be stored for long periods of time in the semi-cured state, so that handling of the prepreg is very easy and the commercial value of the prepreg itself is high. The prepreg can be easily converted to the final cured product simply by heating.

The alicyclic epoxy compound composition (one liquid type) used in the invention can contain other additives in addition to the alicyclic epoxy compound prepared by the epoxidation of the alicyclic polybasic carboxylic ester and the latent curing agent. It is effective to add a phenoxy resin to improve the water resistance of the cured product prepared from the prepreg containing the composition.

The phenoxy resin can be a conventional epoxy resin having a relatively high molecular weight prepared by the polycondensation of bisphenol and epichlorohydrin (15,000–100,000 number average molecular weight by Vapor Pressure Osmometry and 75°–120°C softening temperature). When the phenoxy resin is added to the composition, the arc resistance and tracking resistance of the cured product decreases because of the presence of aromatic rings in the phenoxy resin. However, if the addition of the phenoxy resin is small, the water resistance of the product is substantially improved and the decrease in the arc resistance and tracking resistance can be neglected. The amount of the phenoxy resin employed is usually 1 – 40 parts by weight, preferably 2 – 30 parts by weight, especially 5 – 20 parts by weight to 100 parts by weight of the alicyclic epoxy compound.

In the invention, it is effective to add an alicyclic epoxy compound having at least one 1, 2-epoxy group situated in a 5 or 6 membered ring or an alicyclic epoxy compound having a glycidyl group, such as the following.

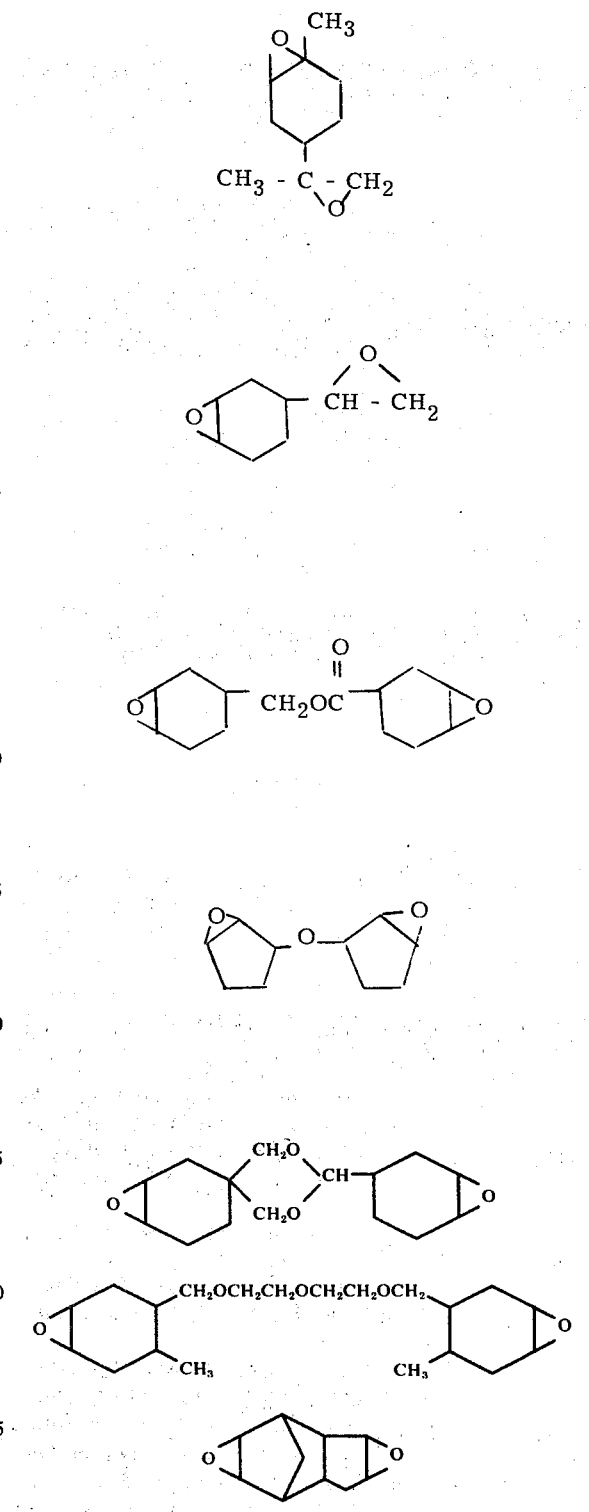

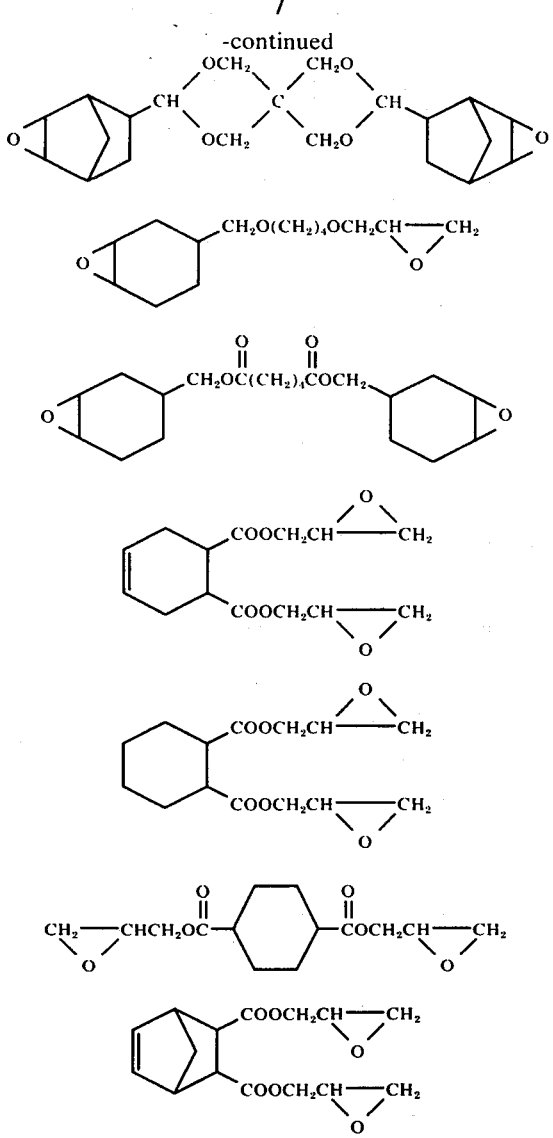

When one of the epoxy compounds is added to the composition, the viscosity of the composition can be adjusted and the impregnation of the composition into the fibrous substrate becomes easier. Also, control of the heat treatment for the B-stage curing operation after impregnation of the composition becomes easier. Moreover, when the prepreg in the B-stage cured state is molded under pressure to prepare the final cured product, the green color of the prepreg is enhanced by the addition of the epoxy compound. Another advantage gained is that the adhesiveness between the prepregs in forming the laminated products is substantially improved.

The latter alicyclic epoxy compound is usually added in amounts of 5 – 100 parts by weight, preferably 10 – 70 parts by weight per 100 parts by weight of the alicyclic epoxy compound derived from the alkadiene alcohol.

In the scope of the invention, it is possible to add a pigment, a thixotropic agent, flame retardant, internal release agent or the like to the prepreg composition. The laminated products or molded products prepared by laminating or molding the electrical insulating prepregs in the form of plates, tubes, rods, or other shapes, and heating the shaped material under pressure, have excellent thermal resistance, mechanical strength, electrical insulating properties, especially arc resistance and tracking resistance, and can be used in various applications such as insulating plates, insulating tubes, insulating support rods, slot wedges, and insulating spacers. It is also possible to prepare electrically insulated conductors or coils having excellent characteristics by covering the electrically insulating prepregs on electrical conductors or inserting the prepregs between plain or foil conductors and heating the composite under pressure.

Having generally described this invention, a further understanding can be obtained by reference to certain specific examples which are provided herein for purposes of illustration only and are not intended to be limiting unless otherwise specified.

REFERENCE EXAMPLE 1

Preparation of the Octadiene Alcohol Ester of Hexahydrophthalic Acid (Preparation of octadienyl hexahydrophthalate)

In a 1 liter four-necked flask equipped with a thermometer, a condenser, a nitrogen gas inlet and a stirrer, 378 g (3.0 mole) of 2,7 - octadienol - 1, 154.2 g (1.0 mole) of hexahydrophthalic anhydride, 100 ml of xylene and 0.5 g of zinc acetate 2-hydrate were charged. The mixture was heated at 120°-150°C for 3 hours under a flow of nitrogen gas, and then further heated at 205°C for 24 hours to remove water.

During the reaction, the stoichometric amount of water of about 18 g was removed. After the reaction, unreacted 2,7 - octadienol - 1, xylene and a small amount of by-product 1,7 - octadienol - 3, were removed by the distillation. The reaction mixture was further heated at 150°C, under a reduced pressure of 1 mmHg to remove the by-product dioctadienyl ether, whereby 392 g of the di (2,7 - octadienol - 1) ester of hexahydrophthalic acid were obtained. The resulting compound was identified by elemental analysis, infrared spectrography.

REFERENCE EXAMPLE 2

Preparation of the Octadiene Alcohol Ester of Tetrahydrophthalic Acid

In a 1 liter glass autoclave equipped with a thermometer, a condenser, a nitrogen gas inlet and a stirrer, 378 g. (3.0 mole) of 2, 7 - octadienol - 1, 152 g. (1.0 mole) of tetrahydrophthalic anhydride, 100 ml. of xylene and 0.5g. of zinc acetate 2 - hydrate were charged. In accordance with the process of Reference Example 1, 388 g of the di-(2, 7 - octadienol - 1) ester of tetrahydrophthalic acid was obtained as the product.

REFERENCE EXAMPLE 3

Epoxidation of the Octadiene Alcohol Ester of Hexahydrophthalic Acid

In a 2 liter three-necked flask equipped with a thermometer, a dropping funnel and a stirrer, 388 g. (1.0 mole) of the di (2,7 -octadienol - 1) ester of hexahydrophthalic acid produced in Example 1 and 1230 ml. of chloroform were charged. A 484 g. (2.54 mole) amount of peracetic acid (40%) was added dropwise through the dropping funnel with stirring over a 2 hour period. The dropping rate was controlled with cooling to keep the temperature below 30°C and then the mixture was stirred at 30°C for 4 hours after the addition of the acid.

After the reaction, the reaction mixture was washed with water to completely remove residual peracetic acid, acetic acid and hydrogen peroxide. The chloroform phase was condensed and dried under reduced pressure whereby 405 g. of the product epoxy compound was obtained. Analysis of the product by the $Et_4NBr-HClO_4$ method, showed that the epoxy value of the product was 0.48 equivalent per 100 G. Analysis of the product by the phenylisocyanate method showed a hydroxyl value of the product of 0.04 equivalent per 100 g. The viscosity of the product at 20°C was 1550 centi-poises.

REFERENCE EXAMPLE 4

Epoxidation of the Octadiene Alcohol Ester of Hexahydrophthalic Acid

The procedure of Example 3 was followed except that 807 g (4.37 mole) of 41.2% peracetic acid was used instead of 40% peracetic acid. The drop rate was controlled by cooling and keeping the temperature below 40°C. The mixture was stirred at 35°C for 3.5 hours after the addition whereby 410 g of an epoxy compound having an epoxy value of 0.65 – 0.67 equivalent per 100 g, a hydroxyl value of 0.081 equivalent per 100 g, and a viscosity (at 20°C) of 2700 centi-poises was obtained.

REFERENCE EXAMPLE 5

Epoxidation of the Octadiene Alcohol Ester of Tetrahydrophthalic Acid

In the 2 liter three-necked flask of Example 3, 386 g (1.0 mole) of the di (2,7 - octadienol - 1 ) ester of tetrahydrophthalic acid and 1230 g of chloroform were charged. An 840 g (4.34 mole) amount of peracetic acid (39.3%) was added dropwise through the dropping funnel with stirring over a 2 hour period. The drop rate was controlled with cooling in order to keep the temperature below 40°C. Subsequently, the mixture was stirred at 40°C for 4 hours after the addition. Thereafter, the process of Example 3 was followed whereby 410g of the epoxy compound having an epoxy value of 0.76 – 0.80 equivalent per 100 g, a hydroxyl value of 0.072 equivalent/100 g and a viscosity (20°C) of 3000 centi-poises was obtained.

The epoxy compounds, the epoxy values, the epoxy equivalents, and the preparation of epoxy compunds used in the Examples are shown in Table 1.

Table 1

| Epoxy compound | Preparation | Property | |
|---|---|---|---|
| | | Epoxy value (equivalent/100g) | Epoxy equivalent (g./mole) |
| ADE-a | Reference 5 | 0.76–0.80 | 125–132 |
| ADE-b | Reference 4 | 0.65–0.67 | 150–154 |
| ADE-c | Reference 3 | 0.48 | 210 |
| Epikote 828 (trade name Shell Chemical Co.) | diglycidyl ether produced by condensation of bisphenol A and epichlorohydrin. | 0.54 | 185 |
| CX-221 (trade name Chisso Co.) | [structure] | 0.73 | 137 |
| CX-205 (trade name Chisso Co.) | [structure] | 1.00 | 100 |
| CX-206 (trade name Chisso Co.) | [structure] | 1.30 | 77 |
| Epikote 191 (trade name Shell Chemical Co.) | [structure] | 0.67 | 149 |
| Epikote 190 (trade name Shell Chemical Co.) | [structure] | 0.62 | 161 |
| Phenoxy resin PKHH (trade name U. C. C.) | high condensate of bisphenol A and epichlorohydrin | 0 softening temp. 80°C molecular weight 20,000 | ∞ |

Table 1-continued

| Epoxy compound | Preparation | Property | |
|---|---|---|---|
| | | Epoxy value (equivalent/100g) | Epoxy equivalent (g./mole) |
| CX-289 (trade name Chisso Co.) | [structure: CH₂OC(CH₂)₄COCH₂ bridging two epoxycyclohexane groups] | 0.45 | 220 |
| CY-175 (trade name Ciba-Geigy) | [structure with CH₂O-CH-CH₂O bridging two epoxycyclohexane groups] | 0.65 | 153 |
| CY-175 HHPA | [structure of CY-175 with additional hydroxyl cyclohexane group]<br><br>[structure showing reaction product]<br><br>Reaction product of hexa-hydrophthalic acid with Cy-175 | 0.45 softening temp. 59°C molecular weight 480 | 220 |

The following test methods for the prepregs were used in the Examples.

A. Tackiness

An absorbent cotton pad having a diameter of about 2 cm was dropped from 30 cm above the prepreg sample at room temperature. The prepreg was placed upside down to observe whether or not the absorbent cotton dropped. If the absorbent cotton dropped from the prepreg, the prepreg was considered to be nontacky.

B. Greenness

Eight sheets of prepregs were plied and cut as regular squares 15cm × 15 cm and the weight was measured. The sheets of prepregs were pressed at 175°C under a high pressure of 70 kg/cm² for 15 minutes to form a laminate. The resin which was squeezed from the sides was cut off and the weight of te laminate was measured. The extent of greenness was given by the equation $$\text{Greenness (\%)} = \frac{\text{(weight of prepregs)} - \text{(weight of laminate after cutting squeezed resin)}}{\text{weight of prepregs}} \times 100$$

EXAMPLE 1

| | |
|---|---|
| ADE - a | 100 wt. parts |
| BF₃ - monoethylamine complex | 3 wt. parts |
| Toluene | 20 wt. parts |
| Methyethylketone | 5 wt. parts |
| Total | 128 wt. parts |

The components were mixed at room temperature to form a uniform composition having a viscosity of 100 centi-poises at 20°C. A glass fiber cloth was dipped in the solution, removed and heated at 125°C for 25 minutes to obtain a prepreg A.

The prepreg A was nontacky and had a green color of 2.5%. In order to observe the storage life, the prepreg A was kept at 50°C for 30 days. The prepreg A had a greenness of 2.3% and showed excellent storage life. The glass fiber cloth used in the test was a plain woven fabric (warp and weft of 32 fil./25mm.) having a thickness of 0.13 mm.

EXAMPLE 2

| | |
|---|---|
| ADE - a | 100 wt. parts |
| BF₃ - monoethylamine complex | 3 wt. parts |
| Total | 103 wt. parts |

In the preparation of the composition, 10 parts by weight of ADE - a was admixed with 3 parts by weight of a complex of BF₃ and monoethylamine, and the mixture was kneaded to form a paste. 90 parts by weight of ADE - a was added to the paste and the mixture was mixed to prepare a uniform composition having a viscosity of 3,000 centi-poises at 20°C and of 150 centipoises at 50°C. The glass fiber cloth of Example 1 was dipped in the composition at 50°C and was removed and heated at 125°C for 25 minutes whereby a prepreg B was obtained. The prepreg B was nontacky and had a greenness of 5.0% at the time of preparation and 4.7% after 30 days at 50°C

EXAMPLE 3

| | |
|---|---|
| ADE - a | 100 wt. parts |
| BF$_3$ - piperidine complex | 3 wt. parts |
| Toluene | 20 wt. parts |
| Methylethylketone | 5 wt. parts |
| Total | 128 wt. parts |

The components were mixed at room temperature to prepare a uniform solution having a viscosity of 102 centi-poises at 20°C. The glass fiber cloth of Example 1 was dipped into the solution and was removed and heated at 125°C for 40 minutes whereby a prepreg C was obtained. The prepreg C was nontacky and greenness of 3.5% at the time of preparation and a coloring of 3.4% after 30 days at 50°C.

EXAMPLE 4

| | |
|---|---|
| ADE - b | 100 wt. parts |
| BF$_3$ - monoethylamine complex | 3 wt. parts |
| Toluene | 20 wt. parts |
| methylethylketone | 5 wt. parts |
| Total | 128 wt. parts |

The components were mixed at room temperature to prepare a uniform solution having a viscosity of 105 centi-poises at 20°C. The glass fiber cloth of Example 1 was dipped into the solution and was removed and heated at 125°C for 20 minutes whereby a prepreg D was obtained. The prepreg D was nontacky and had a greenness of 3.1% at the time of preparation and 2.7% after 30 days at 50°C.

EXAMPLE 5

| | |
|---|---|
| ADE - b | 100 wt. parts |
| BF$_3$ - piperidine complex | 5 wt. parts |
| Toluene | 30 wt. parts |
| methylethylketone | 5 wt. parts |
| Total | 140 wt. parts |

The components were mixed at room temperature to prepare a uniform solution having a viscosity of 30 centi-poises at 20°C. A craft paper was dipped into the solution and was removed and heated at 125°C for 3 hours whereby a prepreg E was obtained. The prepreg E was nontacky and had a greenness of 0.8% at the time of preparation and of 0.5% after 30 days at 50°C.

REFERENCE EXAMPLE 6

| | |
|---|---|
| Epikote 828 | 100 wt. parts |
| BF$_3$ - monoethylamine complex | 3 wt. parts |
| Toluene | 30 wt. parts |
| methylethylketone | 5 wt. parts |
| Total | 138 wt. parts |

The components were mixed at room temperature to prepare a uniform solution having a viscosity of 150 centi-poises at 20°C. The glass fiber cloth of Example 1 was dipped into the solution and was removed and heated at 125°C for 40 minutes whereby a prepreg I was obtained. The preprreg I was nontacky and had a greenness of 3.5% at the time of preparation and a coloring of 3.2% after 30 days at 50°C.

REFERENCE EXAMPLE 7

| | |
|---|---|
| Epikote 828 | 100 wt. parts |
| BF$_3$ - piperidine complex | 5 wt. parts |
| Toluene | 35 wt. parts |
| Methylethylketone | 5 wt. parts |
| Total | 145 wt. parts |

The components were mixed at room temperature to prepare a uniform solution having a viscosity of 70 centi-poises at 20°C. A craft paper was dipped into the solution and was removed and heated at 130°C for 50 minutes whereby a prepreg II was obtained. The prepreg II was nontacky and had a greenness of 1.4% at the time of preparation and 1.2% after 30 days at 50°C.

EXAMPLE 6

Sheets of the prepreg A were piled and pressed at 175°C under a pressure of 105 kg/cm$^2$ for 50 minutes whereby a laminated plate A' having a thickness of 3mm was obtained. In the same manner, laminated plates B' – E' having a thickness of 3mm each were prepared from prepregs B – E. The properties of the laminated plates A' – E' are shown in Table 2. It was found that the laminated plates A' – E' possessed excellent tracking resistance and other properties.

REFERENCE EXAMPLE 8

The process of Example 6 was used to prepare laminated plates I' and II' each having a thickness of 3mm from the prepregs I and II. The properties of the laminated plates I' and II' are shown in Table 2. As it is clear from Table 2, the cured products prepared from he prepregs of I and II had inferior tracking resistance and arc resistance and were not suitable as electrical insulating products.

Table 2

| Item | Test method | Example A' | B' | C' | D' | E' | Reference I' | II' |
|---|---|---|---|---|---|---|---|---|
| Thermal deformation temperature (°C) | JISK 6911 | >200 | >200 | >200 | 175 | 170 | >200 | 165 |
| Bending strength Kg/mm$^2$, 20°C | JISK 6911 | 41 | 43 | 41 | 39 | 18 | 45 | 18 |
| strength Kg/mm$^2$, 150°C | | 32 | 32 | 31 | 29 | — | 28 | — |
| Insulating resistance at normal 20°C | JISK 6911 | >2×10$^{13}$ | >2×10$^{13}$ | >2×10$^{13}$ | >2×10$^{13}$ | >2×10$^{13}$ | >2×10$^{13}$ | >2×10$^{13}$ |
| after boiling 2 hrs. at 20°C | JISK 6911 | 1.5×10$^9$ | 2.5×10$^9$ | 2.2×10$^9$ | 1.8×10$^9$ | 9.0×10$^9$ | 2.0×10$^9$ | 9.1×10$^9$ |
| Tracking resistance CTI | IEC method | >600 | >600 | >600 | >600 | >600 | 250 | 230 |

Table 2-continued

| Item | Test method | Example A' | B' | C' | D' | E' | Reference I' | II' |
|------|-------------|-----|-----|-----|-----|-----|------|-----|
| Arc resistance second | JISK 6911 | 151 | 155 | 153 | 162 | 122 | 62 | 24 |
| Thermal resistance after 2 hrs. | JISK 6911 | 180°C OK | 180°C OK | 180°C OK | 180°C OK | 120°C OK | 180°C OK | 120°C OK |

EXAMPLE 7

The prepreg A was wound onto a rod having a diameter of 10 mm and the rod was removed. The prepreg A was inserted into a mold and was pressed at 160°C under a pressure of 105 Kg/cm$^2$ for 60 minutes whereby a laminated rod having a sectional area of 20 mm × 27 mm and a length of 500 mm was obtained which had a bending strength of 21000 Kg at 20°C. Two copper wires were wound about the middle of the laminated rod with a gap of 200 mm to form a pair of electrodes. A potential of 4.2 KV was applied between the electrodes and the tracking resistance was measured by the salt solution spray method of JEM. No tracking breakdown was found by the application of 101 cycles per minute.

EXAMPLE 8

A conductive copper rod having a diameter of 50 mm and a length of 1.2m was heated at 180°C by an infrared lamp. A prepreg A having a width of 1m was wound on the center of the conductive rod to a thickness of 3 mm and the rod was heated while being turned at 180°C for 40 minutes to prepare an electrically insulating conductive rod. An aluminum foil having a width of 100 mm was contacted with the middle portion of the electrically insulating part as an electrode. A voltage was applied between the aluminum foil electrode and the conductive rod at an increasing rate of 1 KV/sec. The dielectric breakdown voltage of the electrically insulating portion was 54 KV.

EXAMPLE 9

Three types of uniform epoxy resin compositions (one liquid type) were prepared by mixing a BF$_3$ - monoethylamine complex with ADE -a, ADE - b and ADE - c in ratios of 3, 1 and 1 PHR parts per hundred parts epoxy resin, respectively.

In the mixture, the BF$_3$ - monoethylamine complex was mixed little by little at room temperature and then stirred and heated to 70°C. The optimum ratios of the latent curing agent were determined from the evaluation of the other test results.

A 150g amount of the epoxy resin composition was charged into a sample bottle having a volume of 200 ml with a cap and kept at room temperature for 6 months maximum to test the stability of the composition. The results are shown in Table 3 wherein the reference character O indicates a fluid condition, Δ indicates a nonfluid condition but the material can be forcibly stirred and X indicates a nonfluid condition such that the composition cannot be forcibly stirred because of the high degree of gelation.

Table 3

| Type of epoxy compound | Stability Test Time in storage at room temperature | | | | | | |
|---|---|---|---|---|---|---|---|
| | 1 week | 2 weeks | 3 weeks | 1 month | 3 months | 4 months | 6 months |
| ADE - c | O | O | O | O | O | O | O |
| ADE - b | O | O | O | O | O | O | O |
| ADE - a | O | O | O | O | O | Δ | Δ |

As it is clear from Table 3, the epoxy resin compositions can be stably stored for at least 3 months at room temperature. A 100 parts by weight quantity of each of the three epoxy resin compositions (one liquid type) was diluted with 20 parts by weight of toluene to decrease the viscosity of the composition. Mica paper was dipped into the solution and was removed. Then, the mica paper was heated at 80°, 100°or 120°C for the time shown in Table 4 whereby a prepreg was obtained.

Table 4

| Type of epoxy compound | Time for heat treatment Temperature | | |
|---|---|---|---|
| | 120°C | 100°C | 80°C |
| ADE - c | 27 | 65 | 137 |
| ADE - b | 20 | 53 | 110 |
| ADE - a | 15 | 35 | 74 |

The semi-cured prepregs obtained in the B-stage were nontaky and stable by themselves, and could be stored at room temperature for a long time. According to the stability tests, the semi-cured prepregs prepared from ADE - c or ADE - b were stable at room temperature for a time longer than 6 months. The prepreg prepared from ADE - a was stable for 4 — 5 months under the same conditions. The cured products prepared by curing the prepregs after 4 months storage had substantially the same properties as those cured products prepared by curing the prepregs without storage.

EXAMPLE 10

The method of Example 1 was followed for the preparation of prepregs except that 4 parts by weight of a BF$_3$ - piperidine complex, 4 parts by weight of a BF$_3$ - morpholine complex or 5 parts by weight of a BF$_3$ - benzylamine complex was added as the latent curing agent instead of 3 parts by weight of a BF$_3$ - monoethylamine complex. Each prepreg obtained was nontacky and stable as in Example 1.

REFERENCE EXAMPLE 9

The method of Example 9 was followed in that 100 parts by weight of each of the three types of commercial alicyclic epoxy compounds CX-221, CX-206 and Epikote 191 were admixed with 5 parts by weight of a $BF_3$-monoethylamine complex whereby fluid, uniform epoxy resin compositions (one liquid type) were obtained. Because the commercial alicyclic epoxy compounds are very heat sensitive, they were added slowly at about room temperature (below 40°C) and dissolved. stability tests were then conducted on the compositions by the procedure of Example 9. The results are shown in Table 5.

Table 5

| Type of epoxy compound | Stability Test Time in storage at room temperature | | | | | | |
|---|---|---|---|---|---|---|---|
| | 1 week | 2 weeks | 3 weeks | 1 month | 3 months | 4 months | 6 months |
| CX-221 | O | O | Δ | X | X | X | X |
| CX-206 | O | Δ | X | X | X | X | X |
| Epikote 191 | O | O | X | X | X | X | X |

As is clear from Table 5, the commercial alicyclic epoxy compounds can be used to prepare a uniform epoxy resin composition (one liquid type) at the time of preparation. However, when the compositions are stored at room temperature for 2 — 3 weeks, gelation of the compositions begins to occur.

Attempts were made to prepare prepregs with mica paper by the procedure of Example 9, except that the three epoxy resin compositions shown above were used. However, when the compositions were heated above 70°C, a severe exothermic reaction resulted and the reaction could not be stopped at the B-stage cured state.

EXAMPLE 11

One hundred parts by weight of ADE - c, 3 parts by weight of $CuCl_2$-2-ethyl 4-methylimidazole complex and 100 parts by weight of dimethylformamide were mixed at room temperature whereby a fluid, uniform epoxy resin composition (one liquid type) was obtained. Stability tests were conducted as described by the procedure of Example 9, except that the resulting composition of this Example was used. The results confirmed that the fluidity of the composition had not changed for 3 months.

The glass fiber cloth of Example 1 was dipped into the composition was removed and heated at 120°C for 13 minutes whereby a nontacky prepreg was obtained.

EXAMPLE 12

A predetermined amount of the phenoxy resin was added to each of ADE - a, ADE - b and ADE - c and each mixture was heated at 150°C with stirring to prepare a uniform mixture. The mixture was cooled at 50°C and a $BF_3$-monoethylamine complex was gradually added to the mixture with stirring at a rate of 5 mole % based on the ADE, whereby a series of uniform epoxy resin compositions (one liquid type) was obtained.

The stability test procedure of Example 9 was followed except that the compositions above were used. The results obtained are shown in Table 6.

Table 6

| Composition Number | Type of epoxy compound | Phenoxy resin PKHH (PHR) | Stability Test Time in storage at room temperature | | | | | | |
|---|---|---|---|---|---|---|---|---|---|
| | | | 1 week | 2 week | 3 week | 1 month | 3 month | 4 month | 6 month |
| 1–1 | ADE-c | 0 | O | O | O | O | O | O | O |
| 1–2 | ADE-c | 5 | O | O | O | O | O | O | O |
| 1–3 | ADE-c | 10 | O | O | O | O | O | O | O |
| 1–4 | ADE-c | 20 | O | O | O | O | O | O | O |
| 1–5 | ADE-c | 30 | O | O | O | O | O | O | Δ |
| 2–1 | ADE-b | 0 | O | O | O | O | O | O | O |
| 2–2 | ADE-b | 5 | O | O | O | O | O | O | O |
| 2–3 | ADE-b | 10 | O | O | O | O | O | O | O |
| 2–4 | ADE-b | 20 | O | O | O | O | O | O | O |
| 2–5 | ADE-b | 30 | O | O | O | O | O | O | Δ |
| 3–1 | ADE-a | 0 | O | O | O | O | O | O | Δ |
| 3–2 | ADE-a | 1 | O | O | O | O | O | O | Δ |
| 3–3 | ADE-a | 2 | O | O | O | O | O | O | Δ |
| 3–4 | ADE-a | 3 | O | O | O | O | O | O | Δ |
| 3–5 | ADE-a | 5 | O | O | O | O | O | O | Δ |
| 3–6 | ADE-a | 10 | O | O | O | O | O | O | Δ |
| 3–7 | ADE-a | 20 | O | O | O | O | O | O | Δ |
| 3–8 | ADE-a | 30 | O | O | O | O | O | O | Δ |
| 3–9 | ADE-a | 40 | O | O | O | O | O | Δ | Δ |

As is clear from Table 6, all of the compositions can be stored stably for at least 3 months.

The glass fiber cloth of Example 1 was dipped in the epoxy resin composition at the time of preparation, and was removed and heated at 120°C for 28 minutes (ADE - c); for 21 minutes (ADE - b) and for 17 minutes (ADE - a), whereby a series of nontacky prepregs was prepared. The sheets of the resulting prepregs were piled and pressed at 100°C for 4 hours and then 150°C for 4 hours under a pressure of 20 Kg/cm² whereby a laminated product having a thickness of 3mm was obtained. The tracking resistance, the greenness and the water resistance of the laminated products were measured. The results are shown in Table 7.

The water resistance was measured by the following method. A laminated product having a size of 50 × 50 × 3mm was dipped into boiling water for 2 hours, and the appearance of the laminated product was observed and classified with regard to the following classification.

Water resistance 1: A portion of the laminated product of more than 15mm from the cut edge to the center changed to a white color and the glass fibers loosened.

Water resistance 2: A portion of the laminated product of more than 5mm from the cut edge to the center changed to a white color and the glass fibers loosened.

Water resistance 3: A portion of the laminated product of more than 1mm from the cut edge to the center changed to a white color and the glass fibers loosened.

Water resistance 4: Essentially no change.

Table 7

Tracking Resistance, Greenness and Water Resistance

| Composition number | Tracking Resistance IEC Method (CTI) | Tracking Resistance DIP Method (KV) | Water Resistance | % |
|---|---|---|---|---|
| 1-1 | >600 | >3.0 | 1 | 2.7 |
| 1-2 | >600 | >3.0 | 3 | 2.9 |
| 1-3 | >600 | >3.0 | 4 | 3.0 |
| 1-4 | >600 | >3.0 | 4 | 3.2 |
| 1-5 | >600 | 2.7 | 4 | 3.3 |
| 2-1 | >600 | >3.0 | 1 | 2.6 |
| 2-2 | >600 | >3.0 | 3 | 2.7 |
| 2-3 | >600 | >3.0 | 4 | 2.8 |
| 2-4 | >600 | >3.0 | 4 | 2.9 |
| 2-5 | >600 | 2.7 | 4 | 3.1 |
| 3-1 | >600 | >3.0 | 1 | 3.1 |
| 3-2 | >600 | >3.0 | 2 | 3.1 |
| 3-3 | >600 | >3.0 | 2 | 3.1 |
| 3-4 | >600 | >3.0 | 3 | 3.1 |
| 3-5 | >600 | >3.0 | 4 | 3.2 |
| 3-6 | >600 | >3.0 | 4 | 3.3 |
| 3-7 | >600 | >3.0 | 4 | 3.4 |
| 3-8 | >600 | 2.7 | 4 | 3.6 |
| 3-9 | >600 | 2.4 | 4 | 3.7 |

As is clear from Table 7, the data confirms that the water resistance of the products is substantially improved without a decrease in the tracking resistance by combination with the phenoxy resin.

EXAMPLE 13

A predetermined amount of the commercial alicyclic epoxy resin or the alicyclic epoxy resin having a glycidyl group was combined with each of the ADE resins. A BF$_3$ - monoethylamine complex was added to the mixture at a rate of 5 mole % to total epoxy groups, and the mixture was heated with stirring to 55°C whereby a series of uniform epoxy resin compositions (one liquid type) were obtained. A glass fiber cloth was dipped into each composition and was removed and heated at predetermined conditions whereby a series of nontacky prepregs was obtained.

The amounts of the epoxy resins, the conditions for providing B-stage curing and the greenness of the prepregs are shown in Table 8.

Table 8

| Epoxy Resin Composition Parts by wt | | | | Conditions for B-stage curing (°C) | (min) | Greenness (%) |
|---|---|---|---|---|---|---|
| ADE-a | 80 | CX-206 | 20 | 100 | 12 | 2.7 |
| ADE-b | 80 | CX-206 | 20 | 110 | 13 | 7.3 |
| ADE-b | 70 | CX-206 | 30 | 110 | 14 | 3.5 |
| ADE-b | 70 | CY-175 | 30 | 110 | 15 | 7.5 |
| ADE-b | 60 | CY-175 | 40 | 110 | 13 | 6.8 |
| ADE-c | 80 | CX-221 | 20 | 80 | 125 | 9.5 |
| ADE-c | 80 | CX-289 | 20 | 100 | 54 | 10.3 |
| ADE-c | 80 | Epikote 190 | 20 | 120 | 13 | 5.0 |
| ADE-c | 80 | CX-205 | 20 | 120 | 10 | 2.5 |

EXAMPLE 14

| | |
|---|---|
| ADE - a | 100 wt. parts |
| 2 - Ethyl - 4 - methyl imidazole | 5 wt. parts |
| Toluene | 30 wt. parts |
| Methyl ethyl ketone | 5 wt. parts |
| Total | 140 wt. parts |

The components were mixed at room temperature to form a uniform composition having a viscosity of 100 centi-poises at 20°C. A glass fiber cloth was dipped into the mixed composition and removed and then heated at 125°C for 50 minutes whereby a prepreg was obtained. The prepreg was nontacky and had a greenness of 3% and 2.7% after 30 days at 50°C.

EXAMPLE 15

| | |
|---|---|
| ADE - a | 70 wt. parts |
| Cy - 175 HHPA | 30 wt. parts |
| BF$_3$ - monoethylamine complex | 2.5 wt. parts |
| benzene | 28 wt. parts |
| Methyl ethyl ketone | 7 wt. parts |
| Total | 137.5 wt. parts |

The components were mixed at room temperature to form a uniform composition. A glass fiber cloth was dipped into the mixed composition and removed. The cloth was then heated at 100°C for 8 minutes or 11 minutes and two prepregs were obtained. The former prepreg was nontacky and had a greenness of 12.3%, and the latter prepreg was nontacky and had a greeness of 7%. Sheets of the prepregs were piled and pressed at 175°C under a pressure of 105 Kg/cm$^2$ for 1 hour whereby a series of laminated plates having a thickness of 3 mm was obtained.

The properties of the laminated plates are as follows:

| | |
|---|---|
| Arc resistance (JIS K 6911) | 135 sec. |
| Tracking resistance (DIP method) | >3 KV. |

Having now fully described this invention, it will be apparent to one of ordinary skill in the art that many changes and modifications can be made thereto without departing from the spirit or scope of the invention as set forth herein.

What is claimed and intended to be covered by Letters Patent is:

1. An electrically insulating prepreg, which comprises:
    a resin composition of an alicyclic epoxy compound prepared by the epoxidation of an alkadiene alcohol ester of an alicyclic polybasic carboxylic acid, wherein said alkadiene alcohol is 2,7-octadienol-1 or 1,7-octadienol-3, a latent curing agent of a Lewis acid amine complex, and a fibrous solid substrate or sheet like solid substrate, wherein said resin composition once it has been applied to said substrate is in the B-stage cured condition and is thereby acetone soluble, thermoplastic and non-tacky.

2. The electrically insulating prepreg of claim 1, wherein the latent curing agent is metal salt complex of imidazole or an organic acid salt or imidazole.

3. The electrically insulating prepreg of claim 1, wherein said fibrous substrate is glass cloth or paper.

4. The electrically insulating prepreg of claim 1, wherein said sheet-like substrate is a mica wrapper or mica paper.

5. The electrical insulating prepreg of claim 1, wherein 0.1 – 20 parts by weight of the latent curing agent is combined with 100 parts by weight of the alicyclic epoxy resin.

6. The electrically insulating prepreg of claim 1, wherein the alicyclic polybasic carboxylic acid is a phthalic acid compound selected from the group consisting of tetrahydrophthalic acid and hexahydrophthalic acid.

7. The electrically insulating prepreg of claim 6, wherein said alicyclic epoxy compound has an epoxy value of 0.3 – 0.9 mole equivalent and a hydroxy value of 0 – 0.2 mole equivalent.

8. The electrically insulating prepreg of claim 1, wherein the resin composition comprises the alicyclic epoxy compound prepared by the epoxidation of an alkadiene alcohol ester of an alicyclic polybasic carboxylic acid, a phenoxy resin and the latent curing agent with said solid substrate.

9. The electrically insulating prepreg of claim 1, wherein said resin composition further comprises an alicyclic epoxy compound containing at least one epoxy group situated in a 5 or 6 membered ring.

10. The electrically insulating prepreg of claim 1, wherein said resin composition further comprises an alicyclic epoxy compound containing a glycidyl group.

* * * * *